US010765844B2

(12) United States Patent
Pisano et al.

(10) Patent No.: US 10,765,844 B2
(45) Date of Patent: Sep. 8, 2020

(54) MEDICAL FLUID DRAINAGE SYSTEM

(71) Applicant: ECOLE POLYTECHNIQUE FEDERALE DE LAUSANNE (EPFL), Lausanne (CH)

(72) Inventors: Marco Pisano, Lausanne (CH); Valentina Triacca, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 374 days.

(21) Appl. No.: 15/516,429

(22) PCT Filed: Sep. 25, 2015

(86) PCT No.: PCT/IB2015/057394
§ 371 (c)(1),
(2) Date: Apr. 3, 2017

(87) PCT Pub. No.: WO2016/055896
PCT Pub. Date: Apr. 14, 2016

(65) Prior Publication Data

US 2018/0229015 A1 Aug. 16, 2018

(30) Foreign Application Priority Data

Oct. 6, 2014 (GB) .................................. 1417623.4

(51) Int. Cl.
*A61M 27/00* (2006.01)

(52) U.S. Cl.
CPC ... *A61M 27/002* (2013.01); *A61M 2202/0405* (2013.01); *A61M 2205/04* (2013.01)

(58) Field of Classification Search
CPC ...... A61M 2202/0405; A61M 2205/04; A61M 27/002
See application file for complete search history.

(56) References Cited

U.S. PATENT DOCUMENTS

| | | | | |
|---|---|---|---|---|
| 3,810,259 A | | 5/1974 | Summers | |
| 4,850,955 A | * | 7/1989 | Newkirk | A61M 27/002 604/9 |

(Continued)

FOREIGN PATENT DOCUMENTS

| | | |
|---|---|---|
| CN | 203694372 U | 7/2014 |
| EP | 0270205 | 6/1988 |

(Continued)

OTHER PUBLICATIONS

Deo, S. V., Ray, S., Rath, G. K., Shukla, N. K., Kar, M., Asthana, S., & Raina, V. (2004). Prevalence and risk factors for development of lymphedema following breast cancer treatment. Indian journal of cancer, 41(1), 8.

(Continued)

*Primary Examiner* — Kai H Weng
(74) *Attorney, Agent, or Firm* — Andre Roland S.A.; Nikolaus Schibli

(57) ABSTRACT

A medical fluid drainage system which may be advantageously used to actively absorb excess fluid from an interstitium in a living host and to transport it from an inlet member 1 in a non edematous body part out of an outlet member 4 via pumps (5, 6, 7) built in series, such as a distal area with functional lymphatic vessels, or directly in a lymphatic vessel, or directly in a blood vessel.

16 Claims, 9 Drawing Sheets

(56) References Cited

U.S. PATENT DOCUMENTS

| | | | | |
|---|---|---|---|---|
| 5,762,599 | A | 6/1998 | Sohn | |
| 5,810,760 | A | 9/1998 | Andrews | |
| 7,901,419 | B2 | 3/2011 | Bachmann et al. | |
| 8,157,792 | B2 | 4/2012 | Dolliver et al. | |
| 8,517,973 | B2 | 8/2013 | Burnett | |
| 2005/0277865 | A1* | 12/2005 | Gharib .............. | A61M 5/14276 604/9 |
| 2009/0099498 | A1* | 4/2009 | Demers ................. | A61M 1/106 604/6.09 |
| 2014/0114227 | A1 | 4/2014 | Zamarripa et al. | |

FOREIGN PATENT DOCUMENTS

| | | | |
|---|---|---|---|
| GB | 2350794 | A | 12/2000 |
| WO | WO2005115502 | A2 | 12/2005 |
| WO | WO2009096852 | A1 | 8/2009 |
| WO | WO2014062679 | | 4/2014 |

OTHER PUBLICATIONS

International Search Report dated Jan. 19, 2016.
Kissell, L. (2010). Lymphedema Diagnosis and Treatment Cost Savings Act. H.E. 4662, 111th Congress, 2nd Session.
Moffatt, C. J., Franks, P. J., Doherty, D. C., Williams, A. F., Badger, C., Jeffs, E., . . . & Mortimer, P. S. (2003). Lymphoedema: An underestimated health problem. Qjm, 96(10), 731-738.
UK Search report dated Mar. 16, 2015.
Written Opinion of the International Search Authority dated Jan. 19, 2016.

* cited by examiner

MEDICAL FLUID DRAINAGE SYSTEM

CROSS REFERENCE TO RELATED APPLICATIONS

The present application is a U.S. national stage application of PCT/IB2015/057394 filed on Sep. 25, 2015 designating the United States, and claims foreign priority to United Kingdom patent application GB 1417623.4 filed on Oct. 6, 2014, the contents of both documents being herewith incorporated by reference in their entirety.

FIELD OF INVENTION

The present invention generally relates to the draining of physiological fluids. More specifically the present invention relates to pump-based drainage systems, capable of absorbing excess fluid distributed in an interstitium (e.g. subcutaneous space) and transporting said fluid to another location such as the bloodstream, directly through a connection to the venous system or indirectly, through the lymphatic system.

BACKGROUND OF THE INVENTION

Edema is the swelling of soft tissues due to accumulation of interstitial fluid. The fluid is predominantly water, but protein and cell-rich fluid can accumulate if there is infection or lymphatic obstruction. The swelling is the result of the accumulation of excess fluid under the skin in the spaces within the tissues. All tissues of the body are made up of cells and connective tissues that hold the cells together. This connective tissue around the cells is known as the interstitium.

The body's organs have interstitial spaces where fluid can accumulate. An accumulation of fluid in the interstitial air spaces (alveoli) in the lungs occurs in pulmonary edema. In addition, excess fluid sometimes collects in what is called the third space, which includes cavities in the abdomen (abdominal or peritoneal cavity—called "ascites") or in the chest (lung or pleural cavity—called "pleural effusion").

Edema results from increased movement of fluid from the intravascular to the interstitial space, or decreased movement of water from the interstitium into the capillaries or lymphatic vessels. Increased movement of fluid from the intravascular to the interstitial space is due to increased capillary permeability that occurs in infections or as the result of toxin or inflammatory damage to the capillary walls. Edema also results from decreased movement of fluid out of the interstitial space into the capillaries or lymphatic vessels due to lack of adequate plasma oncotic pressure as in nephrotic syndrome, protein-losing enteropathy, or starvation. The lymphatic system is responsible for removing protein and white blood cells (along with some water) from the interstitium. Lymphatic obstruction causes these substances to accumulate in the interstitium.

Lymphedema is a highly disabling disease that causes swollen body limbs due to the malfunctioning of the lymphatic system. It can be inherited (primary) or it can be a consequence of cancer treatment (secondary). Moreover, it is widespread in developing countries as a result of filariasis, a disease caused by a parasitic worm infection, transmitted by mosquitoes. Lymphedema affects approximately 140 million people worldwide. Although epidemiologic data are controversial, it is estimated that in the United States around 6.8 million people have developed or have high risk of developing lymphedema. The incidence of lymphedema is estimated to be around 20% for people undergoing invasive cancer surgery, or other invasive surgeries as hip and knee replacement, cellulitis removal and coronary-artery bypass graft.

In normal conditions, lymphatic vessels absorb up to 1.5 liters per day of fluid (lymph) from the peripheral tissues and they bring it back to the blood circulation. If the lymphatic system is damaged, its drainage action is impaired, resulting in the subcutaneous accumulation of fluid in the limbs, and consequent local swelling. The accumulation of stagnant lymph causes in time dermatitis, pain, weight gain, fatigue, tissue fibrosis, loss of mobility, localized immunodeficiency and recurrent infections. Depression often occurs due to the aesthetical impairment.

As of today, lymphedema cannot be cured. However, a series of therapies are commonly performed, based on the combination of decongestion therapy, massages, lymphatic drainage and compression strategies. These treatments do not remove the cause of the problem but aim only at treating the side effects. Indeed, the disease is not cured and the side effects always come back: the patients must undergo lifelong treatments.

One possible solution for lymphedema could be replacing the function of the damaged lymphatic compartment with an implantable medical system. Implantable medical systems suitable for fluid drainage are known per se. For instance, U.S. Pat. No. 8,157,792 describes a wound drainage system for draining fluid from a wound of a patient. The system includes a system that periodically increases and decreases the application of suction at a drain catheter, together with said drain catheter.

WO 2009/096852 describes an implantable drain adapted to move body fluid from one part of the body to another part of the body. The drainage system enables a patient to easily move around while still being attached to the drain. The drainage system comprises a drainage system for pumping body fluid and a connecting tube and is adapted to be implanted inside the body of the patient. The system can pump body fluid from a treatment area to another part of the body where the fluid can be absorbed and transported out from the body in a normal way. The drainage system has a pump comprising a bellow and a motor may be adapted to compress the bellow and move fluid. The motor is advantageously adapted to repeat the compression at suitable time intervals whereby the drainage system is enabled to repeat the sucking and moving of fluid to substantially constantly suck fluid to the other part of the body.

WO 2014/062679 describes a medical system for moving lymphatic fluid. The medical system may include an implantable body having an inlet end region and an outlet end region represented by an implantable tubular member having one or more fluid openings formed therein. The implantable tubular member may be configured to be implanted or partially implanted in or adjacent to the lymphatic system (e.g., within a lymphatic vessel). The lymphedema medical system may also include a pump coupled to the implantable tubular member. A pump member may be positioned between the inlet end region and the outlet end region. The pump member may be configured to draw lymphatic fluid into the implantable body through the inlet end region and transfer lymphatic fluid out from the implantable body through the outlet end region.

Many other medical systems for draining a fluid are known in the art, such as those described in U.S. Pat. Nos. 8,517,973, 5,762,599, 3,810,259, incorporated herein by reference.

Although such systems are suitable for draining fluid from one body area, or body cavity, to another, they would not be able to absorb and transport fluids distributed in an interstitium, as typical of edemas.

Therefore, there is a need for a system which is capable of draining fluid from an extended area and actively pumping it to reach, directly or indirectly, the bloodstream.

SUMMARY OF THE INVENTION

Accordingly, it is an object of the present invention to provide a system that is able to avoid accumulation of fluid in an interstitium (e.g. a subcutaneous space), maintaining tissue fluid homeostasis over time.

It is also an object of the invention to provide a system that actively absorbs a body fluid from multiple openings distributed along the system and that effectively transports such fluid in a desired body location (e.g., subclavian vein, saphenous vein, lymphatic duct).

A further object of the invention is to provide a system which is minimally invasive, easy to implant and that requires no or minimal maintenance.

It is another object of the present invention to provide a system of small size, allowing laparoscopic implantation and no or minimal discomfort for the patient.

A further object of the present invention is to provide a drainage system that allows a tailored drainage action based on specific patient's need.

These objects are achieved thanks to the drainage system and the method as defined in the claims.

Advantageously the input end of the system according to the invention may be introduced in an edematous space and the output end, e.g. the tip of a catheter, may be connected to a non-edematous space, (e.g., a functioning lymphatic vessel or a vein). The draining system is composed by at least two controllable micropumps connected in series, where the number of micropumps, as well as the distance between the micropumps, depends on the extension of the edema.

The idea is to emulate the functioning of the natural draining system: the lymphatic vessels. Multiple functional units, called lymphangions, compose such vessels. Each lymphangion is an actively contracting vessel tract, coupled to a non-return valve. Each lymphangion, when contracting, propels the lymph to the next unit and, when relaxing, drains the fluid from the previous unit and/or from the external space. The lymphangions contract sequentially, allowing the drainage of the interstitial fluid from very large areas through peristalsis.

In an embodiment of the invention, the system comprises several functional units, in turn composed by a micropump and a porous element. Each functional unit is activated by a controller, and the sequential activation of the micropumps allows the drainage of fluid from the affected tissue through peristalsis, maintaining tissue homeostasis over time. This system may avoid the problems related to current therapies of chronic edemas and in particular of lymphedema, such as the need of recurring of classical approaches (e.g., physiotherapeutic sessions, massages, presso-therapies and the use of compression bandages), the aesthetical impairment for the patient and recurring limb infections due to the stagnant lymph.

In one embodiment, the invention provides for a permanently implantable fluid drainage system comprising N implantable pumps connected in series, with N>=2, each having an inlet, an outlet, and an actuator activated by an energy source through a controller; a first porous element connecting an edematous space with the inlet of the first pump; N−1 porous elements implanted in the edematous space, connecting the N pumps in series; and a last tube connecting the output of the last pump with the subcutaneous space of a distal output, wherein the porous elements are characterized by access pores distributed along their surface and wherein the N pumps are activated and coordinated through one or more controllers to provide the suction of the edematous liquid and its movement from the access pores of the porous elements to the output of the last tube.

The implantable drainage system in accordance with the present invention can be placed within the body of a patient at a suitable location depending on the particular treatment. For example, and without limitation, the implantable drainage system may be placed subcutaneously via surgery in an edematous area to be treated. Any suitable surgical technique can be used to implant the drainage system according to the invention, such as for instance laparoscopy. The implantable drainage system may be used to treat any condition involving the distributed accumulation of fluid in an interstitium within the body of a living host, such as for instance lymphedema, chronic venous insufficiency, chronic edema, myxedema, pulmonary edema, periorbital edema, lymphatic filariasis, edema which occur in specific organs as part of inflammations (e.g. in tendinitis or pancreatitis) and the like. In preferred embodiments, the conditions to be treated are lymphedema, chronic venous insufficiency or chronic edema. In a further preferred embodiment, the condition to be treated is lymphedema.

The implantable drainage system may comprise several porous elements having two tubular extremities. The porous elements have a size and a shape specifically adapted to the edematous space to be treated. Said porous elements may have a cylindrical shape, a polygonal shape, a flat shape or any other suitable shape. In one embodiment, the porous element has a tubular shape. The porous elements are characterized by access pores distributed along their surface, allowing the entry of the body fluid to be drained within the implantable drainage system. In a preferred embodiment, the body fluid to be drained may flow through the pores of the porous elements in a unidirectional way, i.e. from the interstitial space to be drained inside the porous element, while the opposite is impeded. In one embodiment, the extremity of the tubular portion of the first porous element which is not connected with the first pumping member (i.e., the distal input) is closed, so that no fluid can flow inside the first porous element from said extremity.

The system may comprise a last tube connecting the output of the last pumping member of the drainage system with the subcutaneous space of a distal output. The extremity of the last tube which is not in contact with the last pumping member of the drainage system (i.e., the distal output) provides for the release of the drained fluid in a distal area, which in one embodiment is a non-edematous subcutaneous area. In preferred embodiments, the distal output of the last tube of the drainage system ends in close proximity to the lymphatic system, or is connected with a lymphatic vessel or with a vein. In an alternative embodiment of the invention, the distal output of the last tube is connected to a tubular member of another implanted drainage system. In one embodiment, the last tube of the drainage system is a catheter. The term "catheter" is used broadly to refer to any suitable tubing or structure that includes a lumen through which body fluids can flow.

The porous elements and the last tube may be constructed of a soft, flexible, biocompatible material. For example, the porous elements may be made of, without limitation, a polymeric material, such as polyethylene, polypropylene, polybutylene, polystyrene, polyurethane, polycarbonate and/or other suitable materials. In various embodiments, the porous elements and the last tube may include an antifouling and/or anti-fibrotic coating of the internal and external surfaces in order to avoid the clogging of the access ports and of the lumen of the tubes.

The pumping members are specifically designed to be easily implanted within the body of a living host and coupled to both the porous elements and/or the last distal tube through an inlet and an outlet. When activated, the pumping members are responsible for the suction of the fluid to be drained (e.g. an interstitial fluid) within the porous elements of the drainage system, thus allowing the drainage of the affected area and the transport of the fluid towards the distal output. The number and the position of the pumping members depend on the area to be treated, and can be therefore tailored based on the special needs of the living host.

In some embodiments of the invention, the pumping members are micropumps comprising a controller element which regulates the functioning or other parameters of the same. In the present disclosure, the term "controller" refers to any system which monitors and physically alters the operating conditions of a given dynamical system. In the frame of the invention, a controller generally controls the functioning of the micropumps by activating/deactivating the associated actuator and determines the fluid flow rate of said micropumps.

In one aspect of the invention, each and every pumping member has an integrated controller. In accordance with various embodiments of the invention, a controller periodically increases and/or decreases application of suction from the pumping members at porous elements. In various embodiments, the controller may control both the magnitude and associated time of the applied suction.

In various embodiments, the controller may receive information from one or more sensors. The one or more sensors may include, for example, a conventional pressure transducer that provides a signal representative of pressure within the porous elements and/or the last tube. Based on the signal received from the one or more sensors, the controller may verify and/or adjust the level of suction generated by the micropumps.

The controller may include, without limitation, a circuit, such as a timer circuit, and/or a Central Processor Unit (CPU) that may include memory and be appropriately preprogrammed or configured to be loaded with an appropriate program. In an alternative embodiment, each pumping member is controlled remotely by a controller implanted subcutaneously in a distal location. A wireless remote control can non-invasively regulate any function of the drainage system. Even more important, several parameters of the drainage system may be programmable by such a remote control.

Each micropump may be driven by an actuator. In the frame of the present disclosure, an "actuator" is any type of motor that is responsible for moving or controlling a mechanism or system. It is operated by a source of energy, typically electric current, hydraulic fluid pressure, or pneumatic pressure, and converts that energy into motion. In at least some embodiment, micropumps of the drainage system can be driven for example by an electromagnetic actuator, by a piezoelectric actuator or by an electrosmotic actuator. The actuators can be provided with an energy source that is chargeable from outside the body.

In one embodiment of the invention, the implanted system may be passive, while the micropumps may be driven by magnetic forces from external actuators. In other embodiments, the energy source supplying the pumps' actuators may comprise an internal energy source, i.e. the energetic source of the system may be incorporated in each micropump. In another variation of the system, the energy source may be an external source outside the body of the living host and the energy may be transmitted telemetrically via inductive coupling to the implanted active elements, such as for instance actuators having a coil. For example, in a particular embodiment the actuators are magnetically coupled to one or more actuators placed outside the body of the living host. Another variation of the system may include a mechanism to retrieve the energy for the implanted active elements from the living body movements. Alternatively, an energy transmitter transmitting energy wirelessly from an external energy source to charge an internal energy source can be envisaged.

The system preferably comprises feedback means for sending information from inside the host's body to the outside thereof to give feedback information related to at least one functional parameter of the system or a physical parameter of the host, thereby optimizing the performance of the system.

Preferred functional parameters to be analyzed are the flow rate or the pressure of the drained fluid. One variation of the system may include a pressure and/or flow sensing element in a feedback loop to regulate the activation of the micropumps. In some embodiments of the invention, at least one pressure sensor and/or at least one flow velocity sensor is connected to at least one of the porous elements and/or the last tube, and the pressure and/or fluid flow rate values measured from the sensors determine the frequency of motion of the actuators.

For example, the sensors can measure pressure or flow rate of the body fluid through the porous elements and/or the last tubular element, and/or other desired measurements associated with body fluid drainage. Pressure sensors can be for instance small electrical sensors positioned along the drainage system.

The implantable drainage system in accordance with the present invention may be available in multiple configurations, depending on the position and of the extension of the edema. For lower limb edema, for example, the catheter connecting the edematous space to the non edematous space may be much longer respect to the case of upper limb lymphedema.

A further object of the present invention is to provide a method for draining excess body fluid from an edematous area to a non-edematous area by using the drainage system described in the present invention. In particular, it is disclosed herewith a method of draining excess fluid from an edematous space to the blood circulation, comprising implanting N pumps, with N>=2, connected in series through N−1 porous elements, an initial porous element and a last tube connecting the output of the last pump with the subcutaneous space of a distal output, and activating the pumps to drain fluid from the edematous space to the lumen of porous elements and to propel the said fluid to the output of the final tube.

In at least some embodiments of the said method, the pumps are activated in an intermitted, asynchronous manner, so that they create a peristaltic pressure wave along the porous elements and the last tube, and they can further be remotely activated. In one embodiment, the edematous space to be drained is a subcutaneous edematous space.

BRIEF DESCRIPTION OF THE DRAWINGS

The present invention will be described in details in the following section, containing the detailed embodiments of the invention, which are presented solely by non-restrictive examples and illustrated by the attached drawings in which.

DETAILED DESCRIPTION OF THE INVENTION

The present disclosure may be understood more readily by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

In one aspect of the invention, the implantable fluid drainage system for distributed edemas is designed to be implanted subcutaneously and to drain fluid accumulated in an interstitium of a living host, actively and continuously transporting it to a distal, non-edematous space.

Figure 1A:
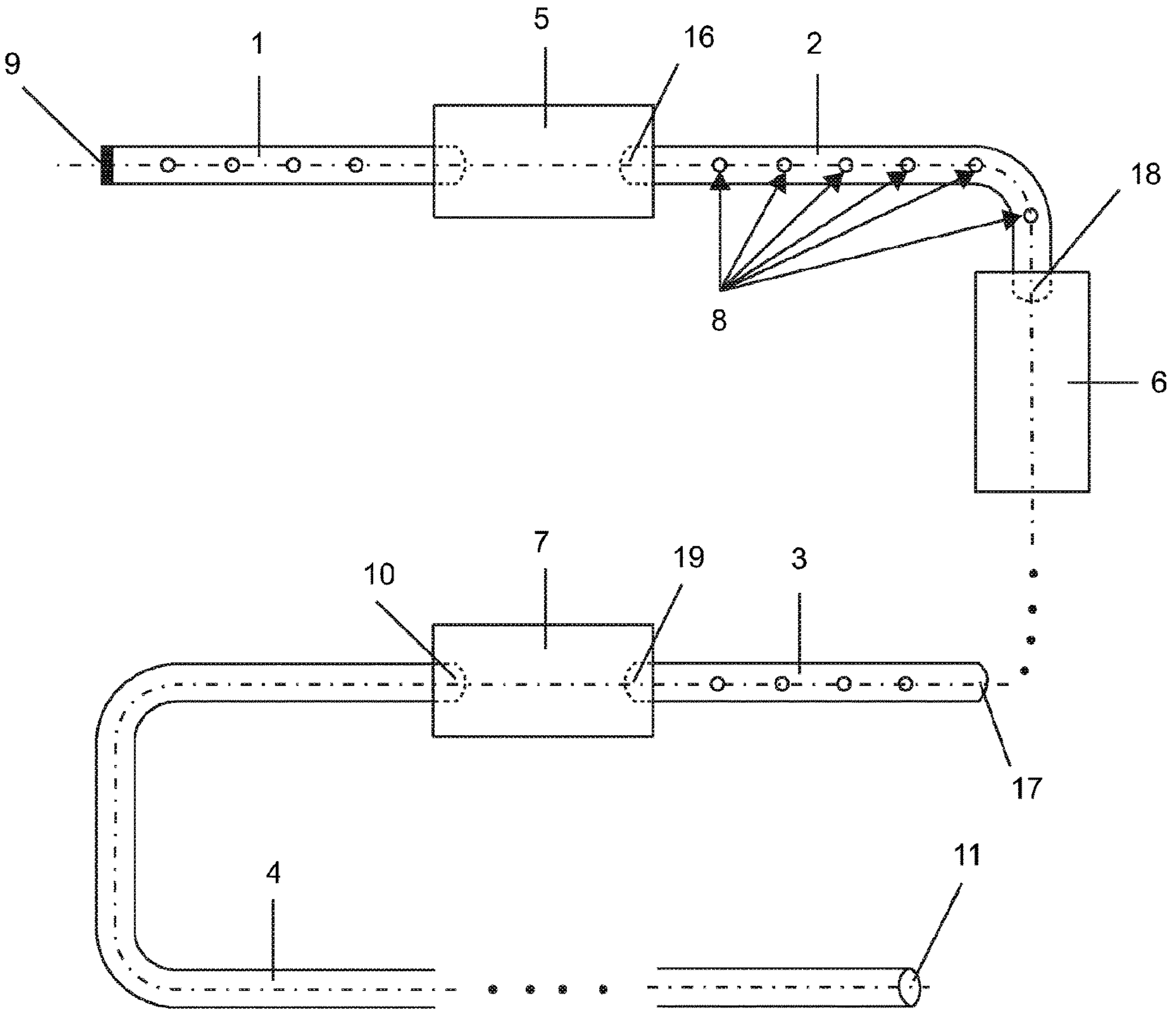
FIG. 1A to 1C show detailed views of the invention according to an embodiment of the implantable system.

FIG. 1A shows a transverse view of the fluid drainage system according to one embodiment of the invention. The system may comprise N pumping members 5, 6, 7 and N+1 porous elements, in form of tubular members, 1, 2, 3, 4. The first N tubular members 1, 2, 3 have multiple accesses pores 8, also referred to as lateral entry points, to their lumen on their lateral surfaces, while the last tubular member 4 has accesses only on its extremities.

Figure 1B:
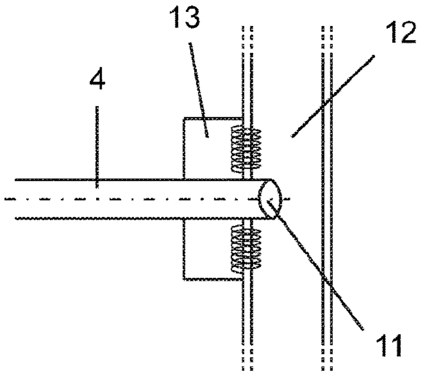
Figure 1C:
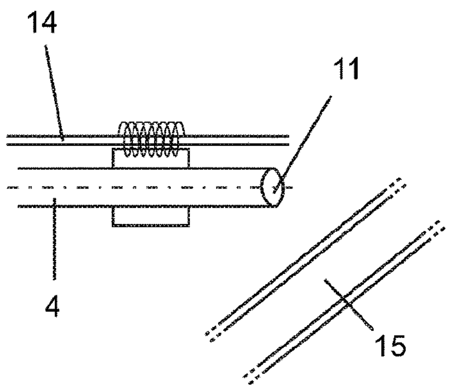

The first tubular member 1 may have one extremity 9 without access, while its other extremity may be connected to the inlet of the first pumping member 5. The last tubular member 4 may have one extremity 10 connected to the last pumping member 7 and the other extremity 11 connected to a non-edematous space forming an exit point. For example, as shown in FIG. 1B, the tubing member 4 could be sutured to a functional vessel 12, which in one embodiment could be a lymphatic vessel or a vein, through the use of a suturable connector 13. In another embodiment of the invention, depicted in FIG. 1C, the tubing member 4 may be anchored to the internal side of the skin 14 in a distal area, where functional lymphatic vessels 15 are present.

As shown in FIG. 1A, the tubular members 2, 3, may have one extremity 16, 17 connected to the outlet of the foregoing pumping member 5, 6, and the other extremity 18, 19 connected to the inlet of the following pumping member 6, 7.

Both the tubular and the pumping members 1, 2, 3, 4, 5, 6, 7 may be coated with an antifibrotic and/or antifouling coating.

Figure 2A:
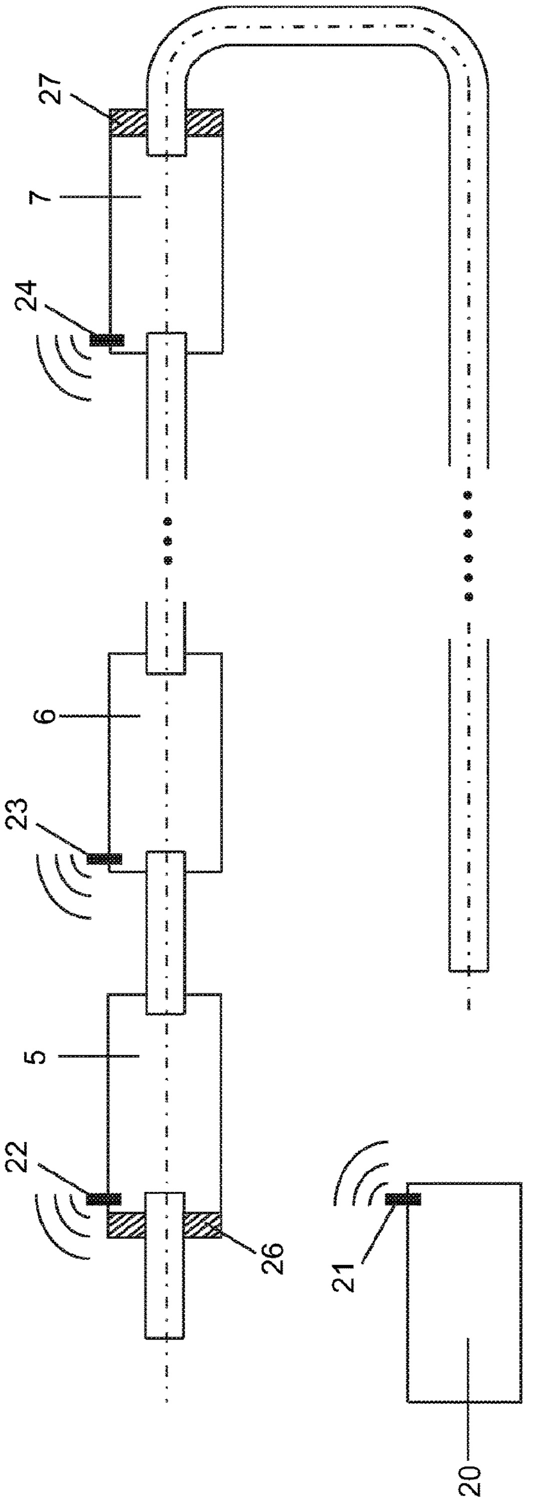
FIG. 2A to 2B show detailed cut views of an embodiment of the fluid drainage system.

The activation of each pumping member may be controlled by a controller unit, as shown in FIG. 2. In a first embodiment, depicted in FIG. 2A, a controller unit 20 may be connected telemetrically with each pumping unit 5, 6, 7 and placed in a distal location, inside or outside the living host. The controller unit 20 will supply the input signals to the pumping units 5, 6, 7 via an antenna 21 and received by dedicated antennas 22, 23, 24 on the pumping units.

At the same time, the pumping units 5, 6, 7 may supply feedback signals to the controller unit 20 via the antennas 22, 23, 24. In an alternative embodiment, shown in FIG. 2B, the controller unit 20 is coupled to the pumping unit 5, 6, 7 via a wire 25.

Figure 2B:
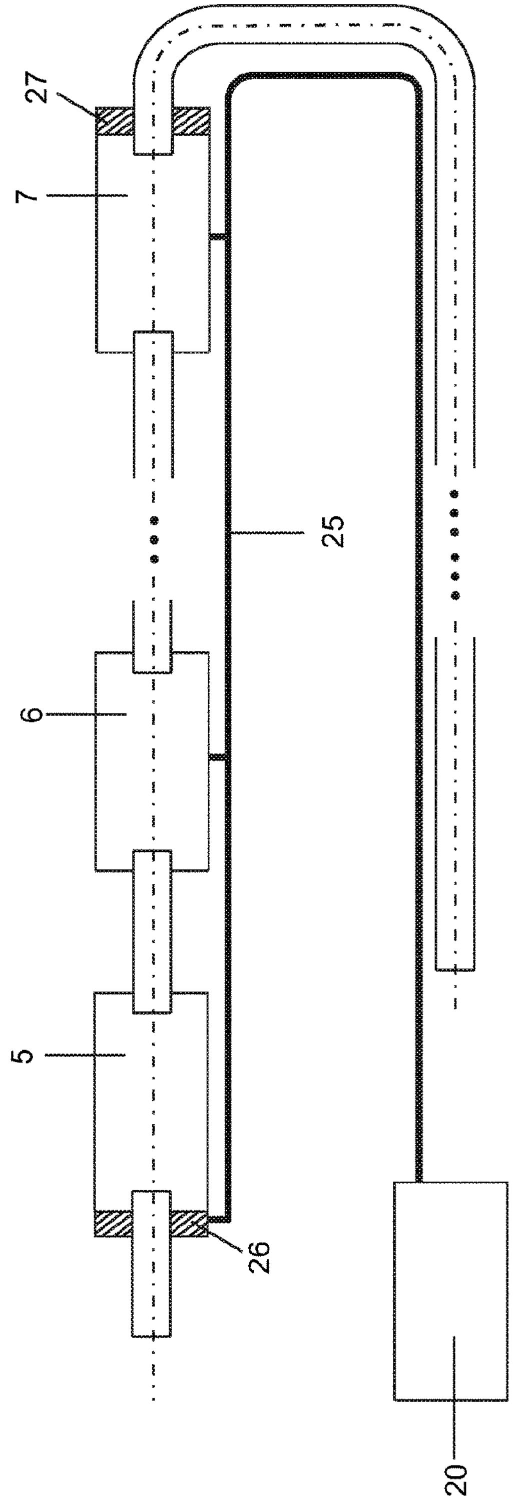

In one aspect of the invention, the controller unit 20 may as well receive inputs by one or more sensors 26, 27, which provide information about the pressure or flow rate in the tubing members. As shown in FIG. 2B, the sensors 26, 27 can be positioned proximate to the outlet or the inlet of the pumping members. In one embodiment, the first sensor 26 can measure the flow rate and/or the pressure within a porous element before it enters the pumping member 5, and the second sensor 27 can measure the flow rate and/or pressure within the proximal portion of the last tube as it exits the pumping member 7. This information can be used to ensure the pumping members generate the desired drainage rate, to monitor patient parameters and/or derive other desired measurements or characteristics. In other embodiments, the drainage system can include more or less sensors. In one embodiment, the sensors 26, 27 may provide said information via the antenna of one or more pumping unit. In an alternative embodiment, the sensor 26, 27 may send the inputs via the wire 25.

Figure 3:
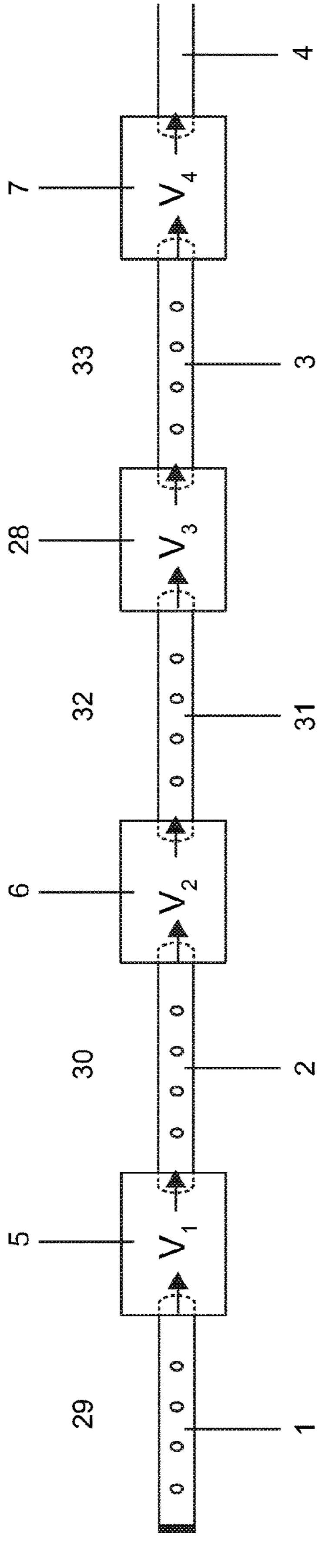
FIG. 3 shows a first possible pumping scheme of the flow drainage system.

The controller 20 may activate and coordinate the pumping members 5, 6, 7, according to different pumping schemes, depending on the desired draining action. FIG. 3 shows a possible pumping scheme in a case in which the number N of pumping members is 4. In a first embodiment, the pumping members 5, 6, 28, 7 are active at the same time, but the provided flow rates V1, V2, V3, V4, are different between each other. In particular, the following relation may be valid: V1<V2<V3<V4. In this way, pumping member 5 drains fluids from the interstitial space 29 through the accesses of the tubing member 1 and move the fluids towards the tubing member 2; pumping member 6 drains from the interstitial space 30 and from the tubing member 2, avoiding the leakage of the fluids pumped by 5 from the accesses of 2, and move the drained fluids towards the tubing member 31; pumping member 28 drains from the interstitial space 32 and from the tubing member 31, avoiding the leakage of the fluids pumped by 6 from the accesses of 31; In the same way, pumping member 7 will drain from the interstitium 33 and from the tubing member 3, moving the fluids towards the tubing member 4, which is without lateral accesses as shown in FIG. 1A.

Figure 4A:
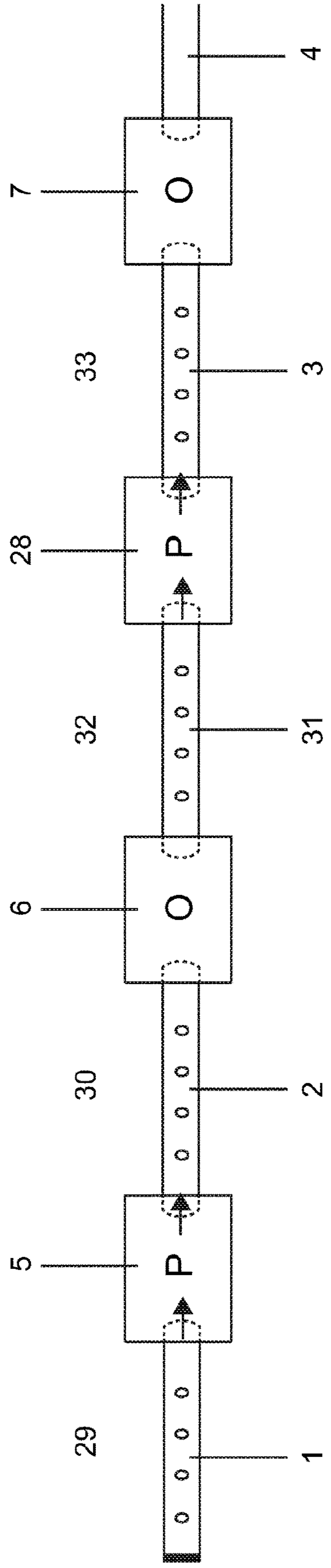
FIG. 4A to 4B show a second possible pumping scheme of the flow drainage system.
Figure 4B:
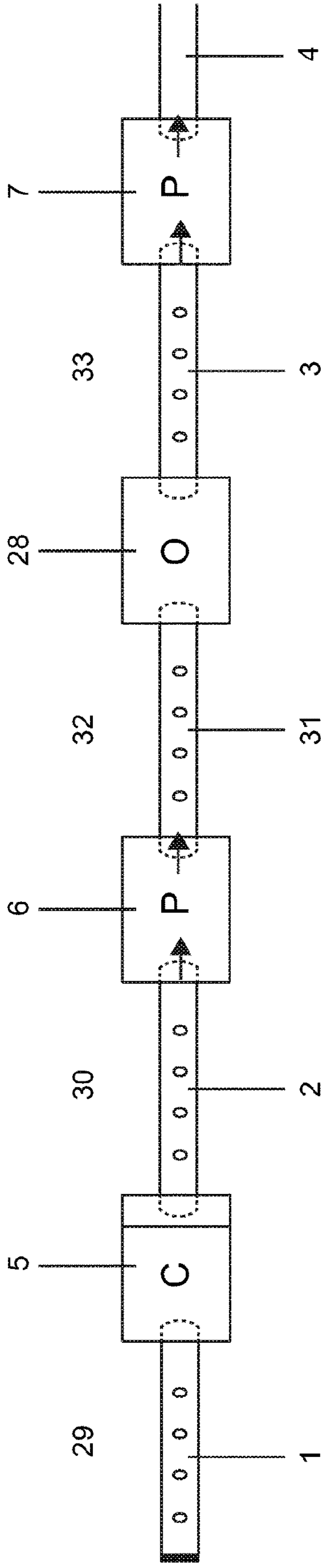
Figure 5A:
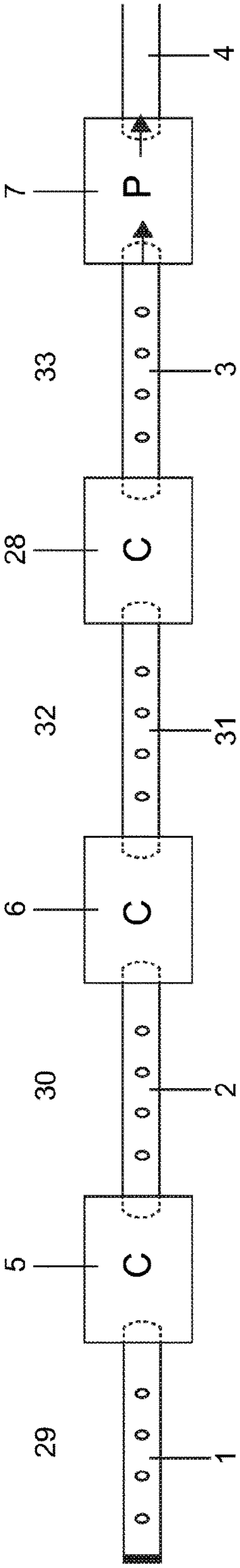
FIG. 5A TO 5H show a third possible pumping scheme of the flow drainage system.
Figure 5B:
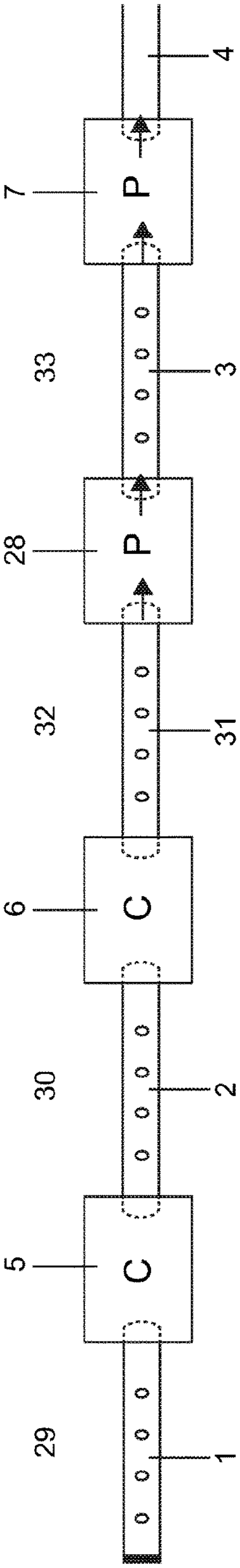
Figure 5C:
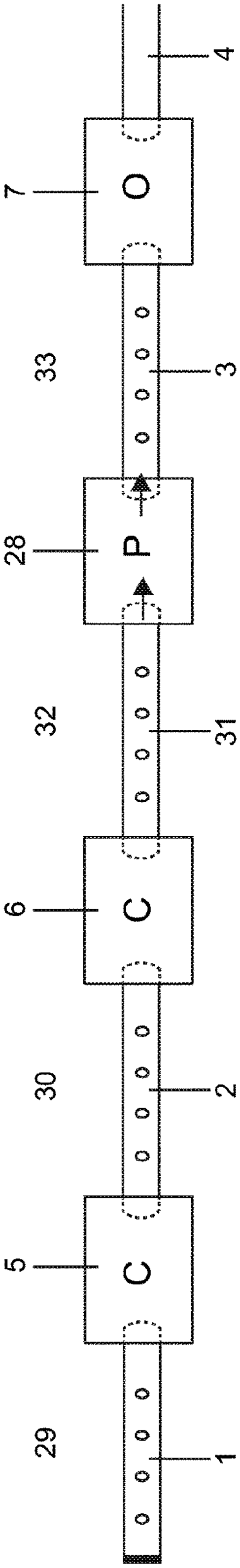
Figure 5D:
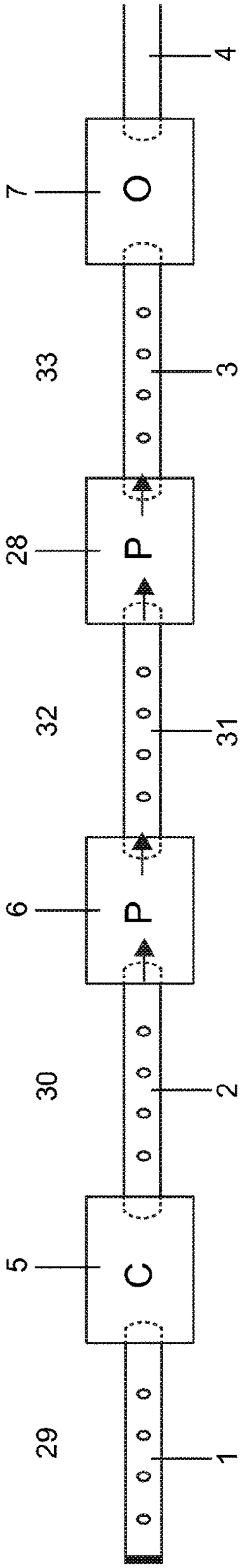
Figures 5E, 5F, 5G, 5H:
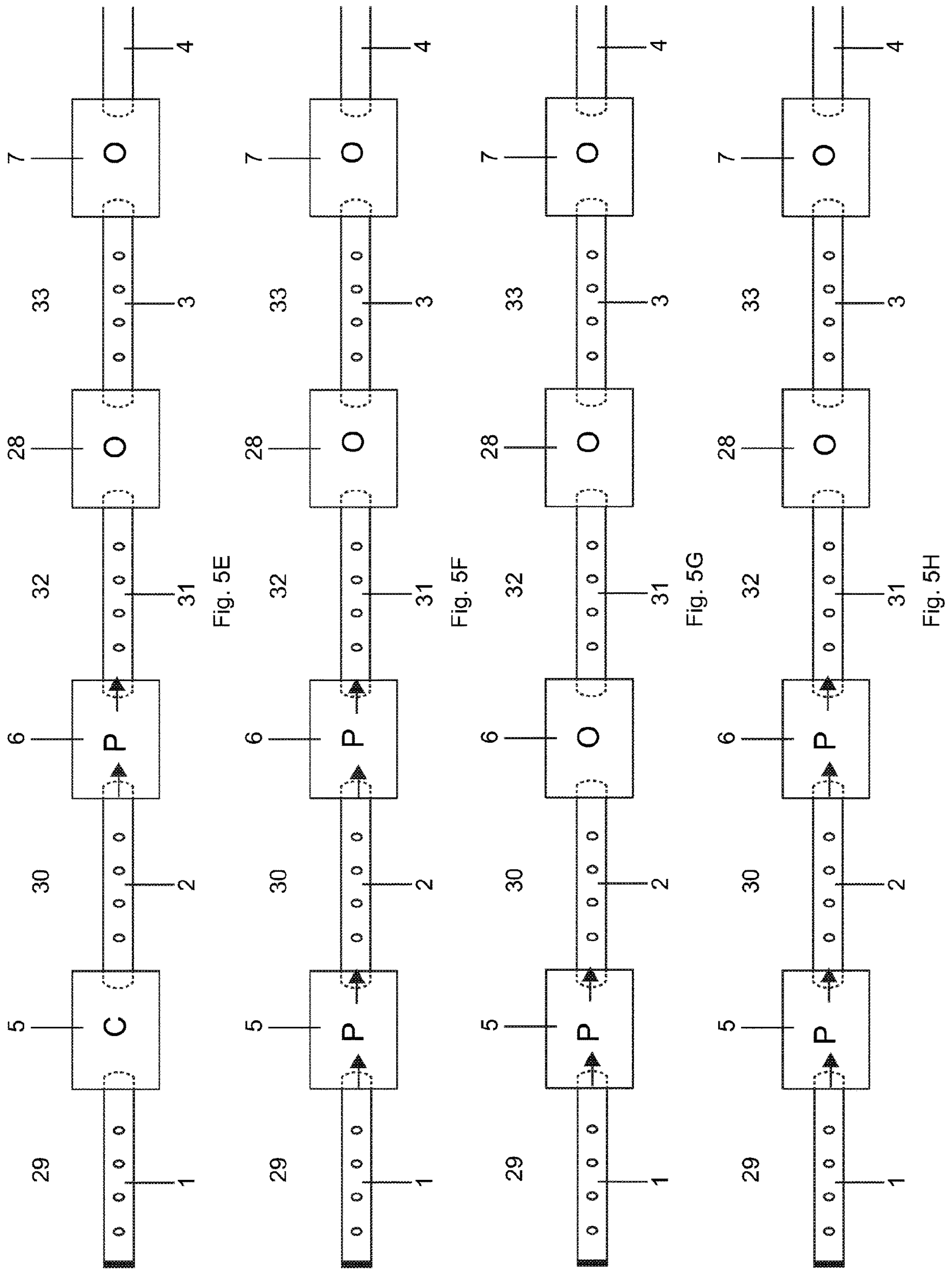

In case the number of pumping member N is equal to 4, another non exclusive example of pumping scheme is shown in FIG. 4. The pumping scheme may be composed of a two step cycle. The first step is schematized in FIG. 4A. Initially, 5 is draining fluid from the interstitial space 29 towards 2; at the same time, 28 is draining fluids from the interstitial space 32 towards 3; meanwhile, 6 and 7 act as an open circuit, allowing the passage of the fluid pumped by 5 and 28. The second step of the cycle is shown in FIG. 4B; pump 5 closes; pumping member 6 drains fluid from 30 and from 2, moving it towards 31; at the same time, 7 drains from 3 and from 33, transporting the fluid in the tubing member 4, while the pumping member 28 is open.

Another non exclusive example of pumping scheme, in case of N equal to 4, is depicted in FIG. 5.

In this case, the pumping scheme will be composed of 7 consecutive steps, shown in FIG. 5A-G. In step 1, shown in FIG. 5A, all the pumping members except 7 will be closed, while pumping element 7 will drain fluid from interstitial space 33 through tubular element 3, transporting it towards the last distal tube 4. In the step 2, shown in FIG. 5B, the pumping member 28 is activated, draining from the interstitial space 32 through tubular element 31 and transporting fluids towards porous tube 3. In step 3, depicted in FIG. 5C, the pumping member 7 is deactivated, remaining open and allowing the passage of fluid due to the pumping action of the pumping element 28. Step 4, schematized in FIG. 5D, contemplate the activation of the pumping member 6, draining from interstitial space 30 through tubular element 2 and pushing fluid towards the porous tube 31. As before, the step 5 (FIG. 5E) consists in the deactivation of 28, which remains open. In step 6 (FIG. 5F), pumping member 5 is activated, draining from the interstitium 29 through the tubing member 1, towards tubing member 2. In the last step, shown in FIG. 5G, pumping member 6 deactivates, remaining open. Next, the cycle continues in the reverse order, with step 6 (FIG. 5H) -5-4-3-2-1. Overall, the described pumping scheme provides suction of fluid from the multiple opening in the tubing member of the draining system, transporting it towards the final tubing member 4 by the formation of a peristaltic wave.

Figure 6A:
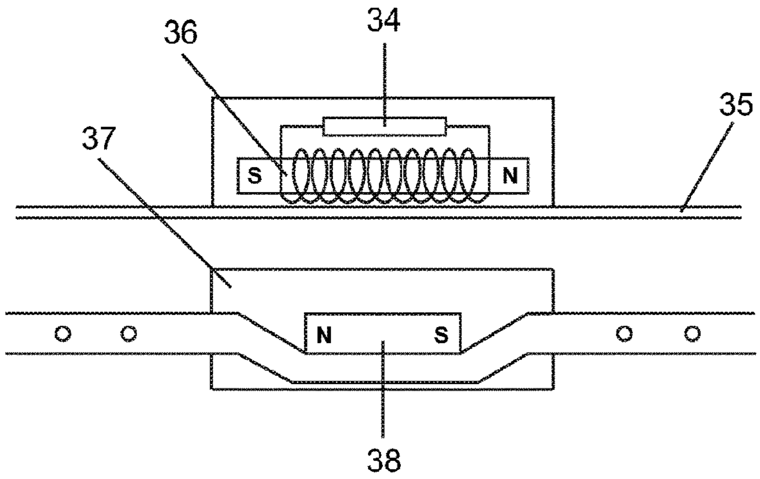
FIG. 6A TO 6C show detailed cut view of embodiments of the power sources and of the pumping units.

The implantable fluid drainage system can be activated by magnetic forces from an external actuator, or by inductive coupling with an external power sources, or by one or more implanted batteries, as shown in FIG. 6. In a first embodiment, shown in FIG. 6A, one or more power sources 34 are outside the skin 35 of the living host. Power source 34 activates an electromagnetic actuator 36, which is outside the body of the living host, although in close proximity with the skin 35 and with the implanted pumping member 37. Pumping member 37 may include a permanent magnet 38. When the electromagnetic actuator 36 is activated and put in movement, it exerts magnetic forces on 38, which moves as well and activates the pumping member 37.

Figure 6B:
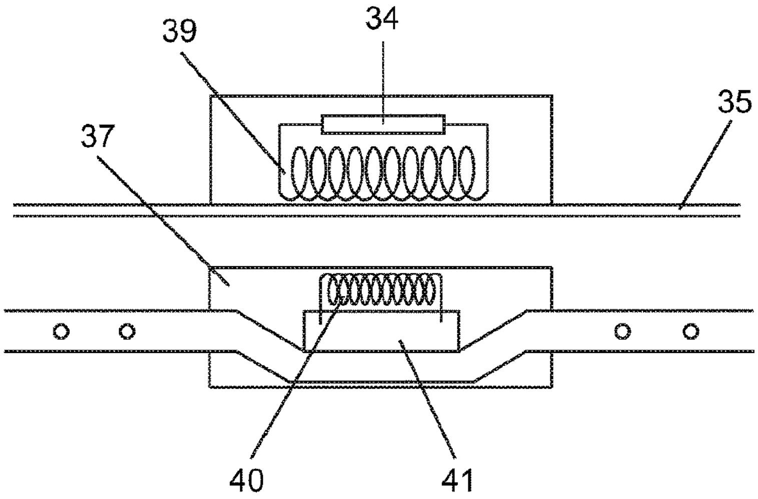

In a second embodiment, shown in FIG. 6B, the power may be transmitted from one external power source 34 to the implanted pumping members 37 via resonant magnetic coupling; a primary magnetic coil 39 may be placed outside 35 and powered by 34. A secondary magnetic coil 40 may be part of the pumping member 37. When activated, magnetic coil 39 transfers energy to 40, which can in turn activate the actuator 41. 41 may for instance be an electromagnetic actuator, or a piezoelectric actuator or an electrosmotic actuator.

Figure 6C:
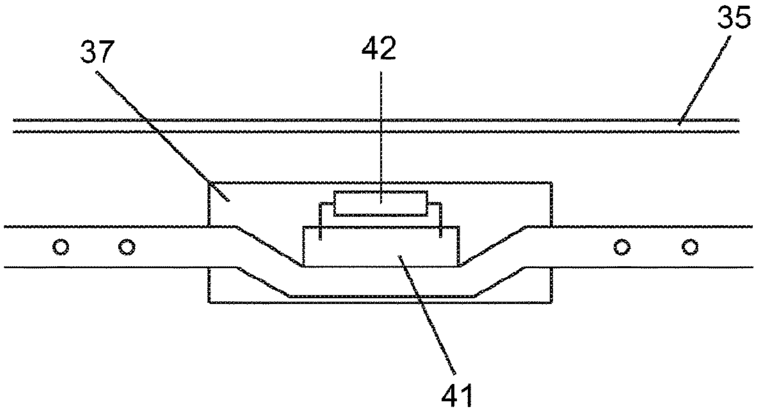

In FIG. 6C is shown a third, non-exclusive embodiment of the invention, in which the energy needed to activate the implanted pumping member 37 may be provided by an implanted battery 42. Battery 42 may be directly connected via wire with the actuator 41.

The implantable fluid drainage system schematized in FIG. 1 may be implanted subcutaneously in areas where there is a distributed accumulation of fluids. Non-exclusive example may be lymphedema-affected upper limbs, lower limbs or male genitalia.

Figure 7B:
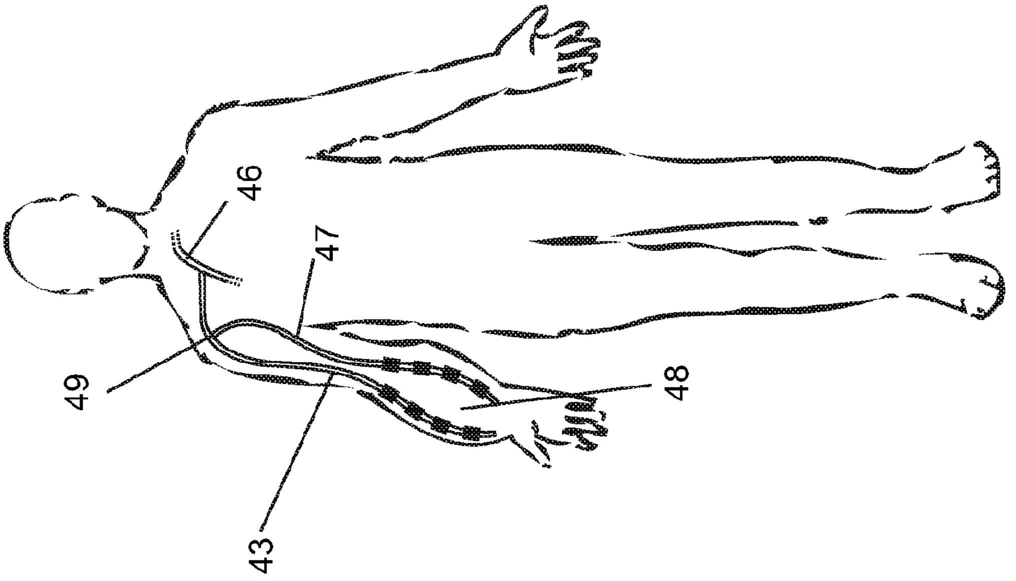
FIG. 7A TO 7B show detailed views of possible configurations and placement of the fluid drainage system in the living host in case of lymphedema at the upper right limb.
Figure 7A:
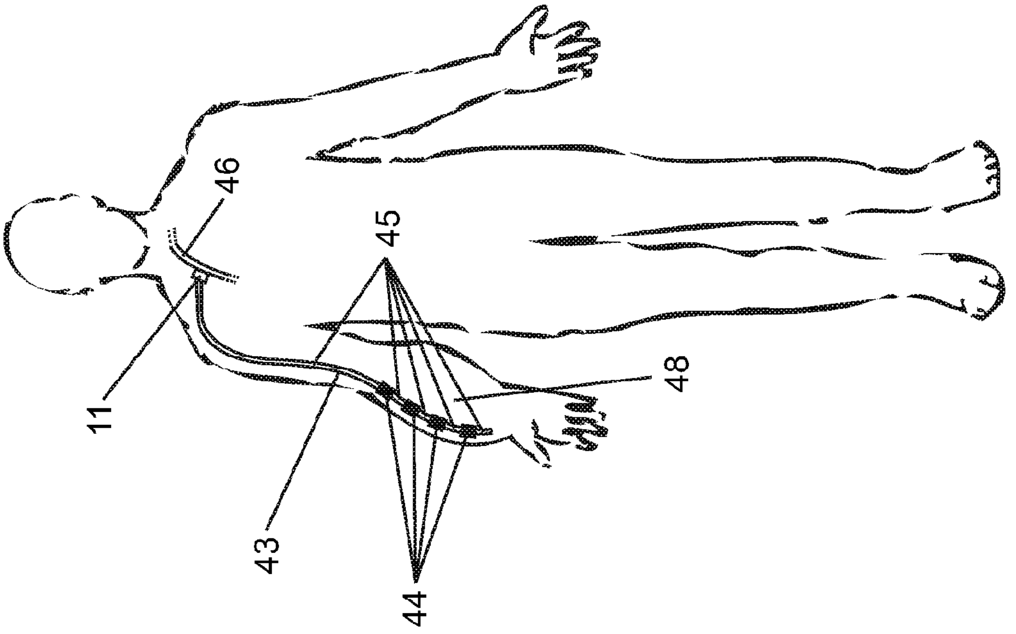

In FIG. 7 two possible placements of the implantable fluid drainage systems in a case of upper right limb lymphedema are shown. FIG. 7A illustrates the placement of a single implant 43 in the subcutaneous space 48 of the right upper limb of the living host. In this example, the implant is composed by 4 pumping members 44 and by 5 tubular members 45. In this example, the final output 11 of the drainage system is sutured to a functional vessel 46 (lymphatic or venous) in the lower neck area.

FIG. 7B schematizes a second possible configuration, in which two drainage systems 43 and 47 are implanted in the edematous area 48. In this example, the additional drainage system 47 is composed by 3 pumping members and 4 tubular members. In this example, the outlet 49 of 47 is connected to the last tubular member of 43.

Figure 8B:
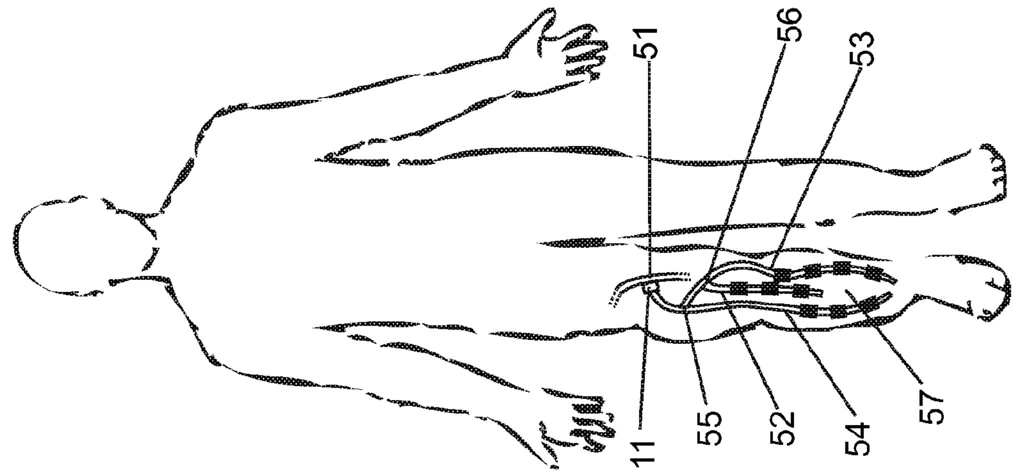
FIG. 8A TO 8B show detailed views of possible configurations and placements of the fluid drainage system in the living host in case of lymphedema at the lower right limb.
Figure 8A:
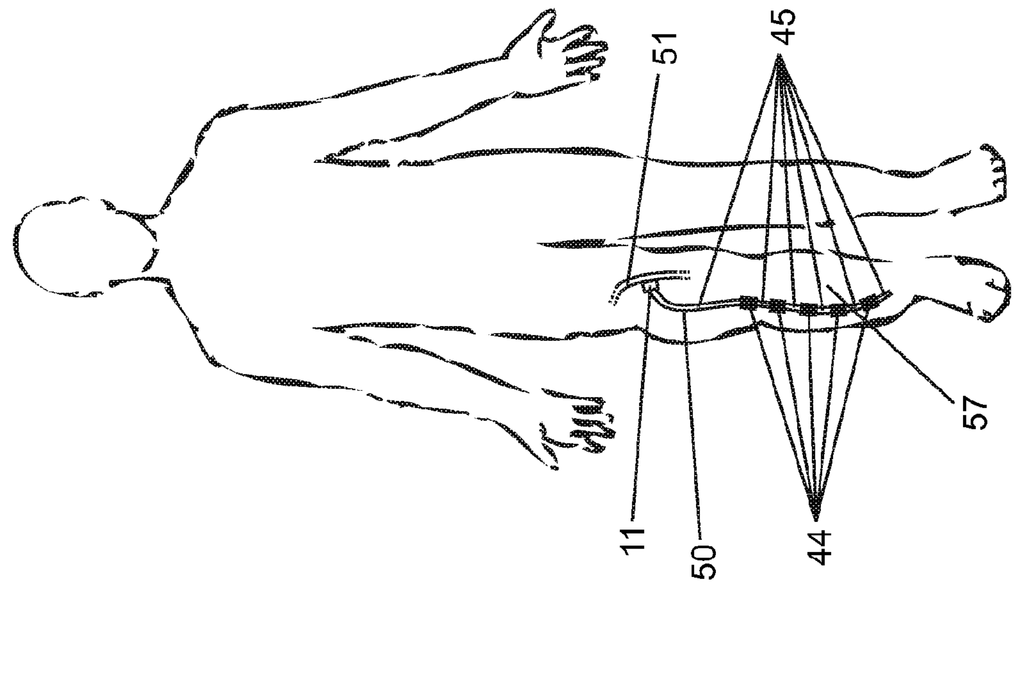

FIG. 8 illustrates two possible placements of the implantable fluid drainage system in case of lower limb lymphedema. FIG. 8A illustrates the placement of a single implant 50 in the edematous area 57. In this example, the implant is composed by 5 pumping members and 6 tubular members 45. In this example, the final output 11 of the system is sutured to the great saphenous vein 51.

FIG. 8B schematize a second possible configuration, in which three drainage systems 52, 53, 54 are implanted in the edematous area 57. In this example, drainage systems 52 and 54 are composed by 3 pumping members and 4 tubular members; drainage system 53 is composed by 4 pumping members and 5 tubular members. In this example, the implant 54 is directly connected to the vein 51 through its output 11; the output 55 of drainage system 53 is connected to 54; the output 56 of drainage system 52 is connected to drainage system 53.

REFERENCES CITED

U.S. Patent Documents

| | | |
|---|---|---|
| 8,517,973 B2 | August 2013 | D. R. Brunett |
| 5,762,599 A | June 1998 | Z. Sohn |
| 7,901,419 B2 | March 2011 | M. Bachmann et al. |

Other Publications

S. Deo et al. Prevalence and risk factors for development of lymphedema following breast cancer treatment. Ind. J. Cancer. Vol. 41(1), pp 8-12 (2004)

C. J. Moffatt et al. Lymphoedema: an underestimated health problem. Q. J. Med. Vol 96, pp 731-738 (2003).

National Lymphedema Network. Lymphedema: diagnosis and treatment cost saving act. 2010.

The invention claimed is:

1. A medical fluid drainage system for draining a fluid from an edematous space of a subcutaneous area of a living body comprising:

N pumps, N being an integer number that is larger or equal to 2, the N pumps connected in series, the integer number N pumps limited by a size of the subcutaneous area for accommodating the N pumps, each having an inlet and an outlet;

a first inlet member connected to the inlet of a first pump;

N−1 inlet members providing fluidic connections between the N pumps;

an outlet member connected to the outlet of a last pump; and a controller configured to provide a coordinated operation of the N pumps to provide for a fluid flow from the first and the N−1 inlet members towards the outlet member, wherein the N pumps, the first inlet member, the N−1 inlet members, and outlet member forming a fluid line, wherein each of the N−1 inlet members includes an entry point configured to allow the fluid to directly enter the fluid line, wherein the outlet member includes an exit point configured to allow the fluid to directly exit the fluid line, and wherein the controller is configured to control the N pumps such that first a pump among the N pumps located the most downstream is activated while remaining pumps of the N pumps are closed, and thereafter repeatedly activating a neighboring pump located upstream while keeping downstream pumps open.

2. The system of claim 1, wherein each one of the N−1 inlet members has a tubular shape, the entry point including a lateral entry point.

3. The system of claim 1, wherein the entry point of each one of the N−1 inlet members includes a porous surface having several entry points.

4. The system of claim 1, wherein the entry point of each one of the N−1 inlet members includes an absorbing surface having several entry points.

5. The system of claim 1, wherein the outlet member has a tubular shape with an open free end forming the exit point.

6. The system of claim 1, wherein the outlet member has a tubular shape with the exit point being laterally arranged.

7. The system of claim 1 configured to drain the fluid from a location within a living body, the fluid being a physiological fluid.

8. The system of claim 7, configured to be partially or totally implantable.

9. The system of claim 1, wherein the outlet member is connected in parallel to a second fluid drainage system.

10. The system of claim 1, further comprising:

an actuator for activating the fluid line;

a pressure or flow sensor connected to at least one of the N−1 inlet members and to the outlet member, wherein a measurement of the pressure or flow rate sensor is used to determine a frequency of motion of the actuator.

11. The system of claim 1, wherein the controller is configured to control the N pumps such that a flow rate of a pump of the N pumps is larger than a flow rate of a respective neighboring pump arranged upstream.

12. The system of claim 1, wherein the controller is configured to operate the N pumps to generate a peristaltic pressure wave along the fluid line.

13. A method of draining excess fluid from an edematous space of a subcutaneous area with a medical fluid drainage system, the system including, N pumps, N being an integer number that is larger or equal to 2, the N pumps connected in series, the integer number N pumps limited by a size of the subcutaneous area for accommodating the N pumps, each having an inlet and an outlet;

a first inlet member connected to the inlet of a first pump;

N−1 inlet members providing fluidic connections between the N pumps; and an outlet member connected to the outlet of a last pump, wherein the N pumps, the first inlet member, the N−1 inlet members, and outlet member forming a fluid line, each of the N−1 inlet members includes an entry point configured to allow a fluid to directly enter the fluid line, and the outlet member includes an exit point configured to allow the fluid to directly exit the fluid line, the method comprising the steps of:

implanting the system in a living host, by positioning the first inlet member in the edematous space and by positioning the outlet member in a non-edematous space; and activating and coordinating the N pumps to drain fluid from the edematous space to the non-edematous space through the fluid line, the activating and coordinating including a controlling of the N pumps such that first a pump among the N pumps located the most downstream is activated while remaining pumps of the N pumps are closed, and thereafter successively activating a neighboring pump located upstream while keeping downstream pumps open.

14. The method of claim 13, further comprising the step of:

providing a specific flow rate with each one of the N pumps depending on a location of each one of the N pumps along the fluid line.

15. The method of claim 13, further comprising the step of:

operating the N pumps to generate a peristaltic pressure wave along the fluid line.

16. The method of claim 13, wherein the step of activating and coordinating the N pumps further comprises:

controlling the N pumps such that a flow rate of a pump of the N pumps is larger than a flow rate of a respective neighboring pump arranged upstream.

* * * * *